US009854991B2

(12) United States Patent
Bzostek et al.

(10) Patent No.: US 9,854,991 B2
(45) Date of Patent: Jan. 2, 2018

(54) INTEGRATED NAVIGATION ARRAY

(71) Applicant: Medtronic Navigation, Inc., Louisville, CO (US)

(72) Inventors: Andrew Bzostek, Boulder, CO (US); Brad Jacobsen, Erie, CO (US)

(73) Assignee: Medtronic Navigation, Inc., Louisville, CO (US)

(*) Notice: Subject to any disclaimer, the term of this patent is extended or adjusted under 35 U.S.C. 154(b) by 451 days.

(21) Appl. No.: 13/833,452

(22) Filed: Mar. 15, 2013

(65) Prior Publication Data
US 2014/0275987 A1    Sep. 18, 2014

(51) Int. Cl.
*A61B 5/05* (2006.01)
*A61B 5/06* (2006.01)
*G01B 21/04* (2006.01)
*G01B 7/00* (2006.01)
*A61B 34/20* (2016.01)
*A61B 90/14* (2016.01)
*A61B 17/00* (2006.01)
*A61B 90/00* (2016.01)
*A61B 90/10* (2016.01)

(52) U.S. Cl.
CPC .............. *A61B 5/061* (2013.01); *A61B 34/20* (2016.02); *A61B 90/14* (2016.02); *G01B 7/003* (2013.01); *G01B 21/042* (2013.01); *A61B 2017/00119* (2013.01); *A61B 2017/00725* (2013.01); *A61B 2034/2051* (2016.02); *A61B 2090/067* (2016.02); *A61B 2090/101* (2016.02)

(58) Field of Classification Search
USPC .................................. 600/407, 424; 606/130
See application file for complete search history.

(56) References Cited

U.S. PATENT DOCUMENTS

| 3,835,861 | A | * | 9/1974 | Kees, Jr. | ................ | A61B 90/14 24/492 |
| 5,300,080 | A | * | 4/1994 | Clayman | ................ | A61B 90/11 604/117 |
| 5,370,118 | A | | 12/1994 | Vij et al. | | |
| 5,528,651 | A | | 6/1996 | Leksell et al. | | |
| 5,577,503 | A | | 11/1996 | Bonutti | | |
| 5,592,939 | A | | 1/1997 | Martinelli | | |
| 5,682,890 | A | | 11/1997 | Kormos et al. | | |

(Continued)

FOREIGN PATENT DOCUMENTS

| EP | 1174082 A1 | 1/2002 |
| EP | 1743591 A2 | 1/2007 |

(Continued)

OTHER PUBLICATIONS

Invitation to Pay Additional Fees dated Jan. 25, 2008 for PCT/US2007/009928 filed Apr. 24, 2007.

(Continued)

*Primary Examiner* — James Kish
(74) *Attorney, Agent, or Firm* — Harness Dickey

(57) ABSTRACT

Disclosed is a method and system for navigating an instrument relative to a configurable theater system. The configurable theater instrument can be any instrument positioned in a theater that is configured to have more than one position. A localizer can generate an electromagnetic field that is sensed by a tracking device to determine a location of the tracking device with the sensed electromagnetic field.

36 Claims, 4 Drawing Sheets

(56) References Cited

U.S. PATENT DOCUMENTS

| | | | |
|---|---|---|---|
| 5,729,129 A | 3/1998 | Acker | |
| 5,871,445 A | 2/1999 | Bucholz | |
| 5,938,599 A | 8/1999 | Rasche et al. | |
| 5,976,156 A | 11/1999 | Taylor et al. | |
| 6,006,126 A | 12/1999 | Cosman | |
| 6,076,008 A | 6/2000 | Bucholz | |
| 6,122,541 A | 9/2000 | Cosman et al. | |
| 6,311,082 B1 | 10/2001 | Creighton, IV et al. | |
| 6,351,662 B1 | 2/2002 | Franck et al. | |
| 6,405,072 B1 | 6/2002 | Cosman | |
| 6,474,341 B1 | 11/2002 | Hunter et al. | |
| 6,493,573 B1* | 12/2002 | Martinelli et al. | 600/424 |
| 6,529,765 B1 | 3/2003 | Franck et al. | |
| 6,618,612 B1 | 9/2003 | Acker et al. | |
| 6,704,957 B2 | 3/2004 | Rhodes | |
| 6,738,656 B1 | 5/2004 | Ferre et al. | |
| 6,774,624 B2 | 8/2004 | Anderson et al. | |
| 6,850,909 B1 | 2/2005 | Aiello et al. | |
| 7,095,732 B1 | 8/2006 | Watson, Jr. | |
| 7,313,430 B2 | 12/2007 | Urquhart et al. | |
| 7,453,804 B1 | 11/2008 | Feroz et al. | |
| 7,583,651 B2 | 9/2009 | Yamada et al. | |
| 7,697,457 B2 | 4/2010 | Igarashi et al. | |
| 7,738,481 B2 | 6/2010 | Igarashi et al. | |
| 7,813,275 B2 | 10/2010 | Yamada et al. | |
| 7,843,817 B2 | 11/2010 | Gong et al. | |
| 7,925,328 B2 | 4/2011 | Urquhart et al. | |
| 7,978,725 B2 | 7/2011 | Gong et al. | |
| 8,301,226 B2 | 10/2012 | Csavoy et al. | |
| 8,311,611 B2 | 11/2012 | Csavoy et al. | |
| 8,467,852 B2 | 6/2013 | Csavoy et al. | |
| 8,844,536 B1* | 9/2014 | Schuele | F16B 2/12 128/845 |
| 2001/0011175 A1 | 8/2001 | Hunter et al. | |
| 2001/0027271 A1 | 10/2001 | Franck et al. | |
| 2003/0097061 A1 | 5/2003 | Ferre et al. | |
| 2003/0187351 A1 | 10/2003 | Franck et al. | |
| 2003/0189948 A1 | 10/2003 | Sashihara | |
| 2004/0147839 A1 | 7/2004 | Moctezuma de la Barrera et al. | |
| 2004/0152972 A1 | 8/2004 | Hunter | |
| 2004/0199072 A1 | 10/2004 | Sprouse et al. | |
| 2004/0215071 A1 | 10/2004 | Frank et al. | |
| 2005/0049486 A1 | 3/2005 | Urquhart et al. | |
| 2005/0085720 A1 | 4/2005 | Jascob et al. | |
| 2005/0198849 A1 | 9/2005 | Goeggelmann et al. | |
| 2008/0097195 A1 | 4/2008 | Urquhart et al. | |
| 2008/0269599 A1 | 10/2008 | Csavoy et al. | |
| 2008/0269602 A1 | 10/2008 | Csavoy et al. | |
| 2009/0201898 A1 | 8/2009 | Gong et al. | |
| 2010/0182925 A1 | 7/2010 | Nagata et al. | |
| 2012/0046542 A1 | 2/2012 | Csavoy et al. | |
| 2013/0147467 A1* | 6/2013 | Engel et al. | 324/207.12 |

FOREIGN PATENT DOCUMENTS

| | | |
|---|---|---|
| EP | 1776923 A1 | 4/2007 |
| EP | 1887309 A1 | 2/2008 |
| EP | 2139419 A1 | 1/2010 |
| WO | WO-0224094 A2 | 3/2002 |
| WO | WO-02098273 A2 | 12/2002 |
| WO | WO-2004100767 A2 | 11/2004 |
| WO | WO-2008130355 A1 | 10/2008 |
| WO | WO-2010133839 A1 | 11/2010 |
| WO | WO-2012109760 A1 | 8/2012 |
| WO | WO-2013013718 A1 | 1/2013 |

OTHER PUBLICATIONS

International Search Report and Written Opinion dated Mar. 26, 2008 for PCT/US2007/009928 filed Apr. 24, 2007.I.

International Preliminary Report on Patentability dated Nov. 5, 2009 for PCT/US2007/009928 filed Apr. 24, 2007.

International Search Report and Written Opinion dated Aug. 7, 2014 for PCT/US2014/026364 claiming benefit of U.S. Appl. No. 13/833,452, filed Mar. 15, 2013.

International Preliminary Report on Patentability and Written Opinion dated Sep. 24, 2015 for PCT/US2014/026364 claiming benefit of U.S. Appl. No. 13/833,452, filed Mar. 15, 2013.

* cited by examiner

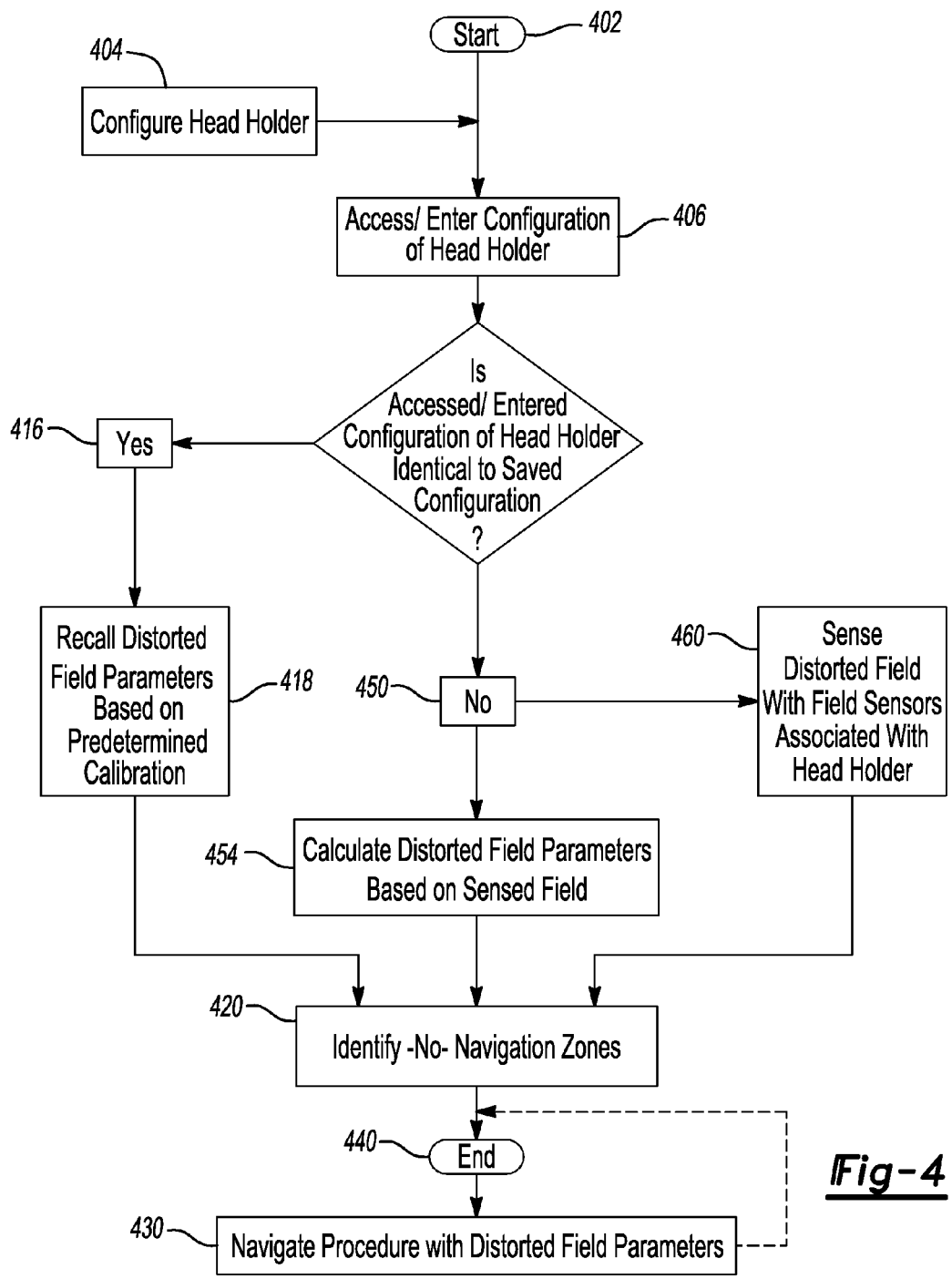

INTEGRATED NAVIGATION ARRAY

FIELD

The subject disclosure is related generally to a navigated procedure on a subject, and particularly to a navigated procedure on a subject with a predetermined distortion of an electromagnetic field.

BACKGROUND

This section provides background information related to the present disclosure which is not necessarily prior art.

In performing a procedure, a user, such as a surgeon, can perform a procedure on a subject with a navigation system. The navigation system can assist in determining a location of a tracked device, such as a scalpel, catheter, or deep brain stimulation probe, by tracking a tracking device associated with the tracked device. The tracked device can include the instruments noted above, to which a tracking device is associated, such as directly affixed thereto. The instrument can allow a procedure to be performed on a subject while illustrating the location of the instrument relative to the subject. The position of the instrument can be illustrated relative to the subject by superimposing an icon representing the instrument on an image of the subject.

Image data is often acquired of the subject for display prior to, during, and after a procedure on the subject. The image, including the image data which generates or is used to render the image, can be registered to the subject. The image data can define an image space that can include a three-dimensional space. The subject can likewise define a three-dimensional space physical space to which the image data is registered. Registration can be performed in a plurality of processes.

According to various embodiments, a navigation system can use an electromagnetic navigation system (EM navigation system) to acquire or determine the navigation information. In an EM navigation system, an electromagnetic field (EM field) is generated by a localizer and sensed by a tracking device. The localizer can be positioned relative to the subject space and a tracking device can be associated or positioned on the instrument or vice versa. According to various embodiments, a localizer can be positioned on the instrument that can generate the EM field to be sensed by a tracking device positioned away from the instrument. It is understood that the EM field can be affected by conducting materials, such as metals or other conducting materials (e.g., conducting polymers or impregnated polymeric materials or devices) and/or magnetic materials (e.g. ferromagnetic materials).

SUMMARY

This section provides a general summary of the disclosure, and is not a comprehensive disclosure of its full scope or all of its features.

A navigation system can include an EM navigation system where an EM field is generated by a localizer. The EM field generated by a localizer can be affected by various materials, such as conducting or magnetic materials, within the volume where navigation is to occur. The distortion of the EM field can affect sensing of the EM field by a tracking device that senses the EM field. As discussed further herein, the EM field is sensed by a tracking device to determine its location within the field relative to the localizer. Accordingly, distortions generated within the EM field can affect accuracy of navigation of the tracked device. Also, the shape, geometry, and magnetic features of materials can effect distortion. Cuts or breaks in structures can minimize eddy current loops to minimize distortion. Also, inducing constant saturating magnetization can reduce ferromagnetic induced distortions. By knowing or determining the type of distortion, the EM field can be determined to ensure accurate navigation throughout a volume, even when a distorting material is within the field. The field can be determined based upon selected distorting elements, such as a holding or mounting frame, at various times. For example, a software algorithm can be implemented to determine the location of various portions of the mounting frame to determine the appropriate distortion based upon calculated or predetermined distortion effects. Additionally, factory calibration, such as during manufacturing of a holding frame and/or a localizer, can be implemented to be determined and no distortion of a generated EM field. According to various embodiments, the distorted field can be determined and calibrated to ensure an accurate navigation of an instrument during a procedure.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 4 is a flowchart of a method of determining a distorted navigation field.

Corresponding reference numerals indicate corresponding parts throughout the several views of the drawings.

DETAILED DESCRIPTION

Figure 1:
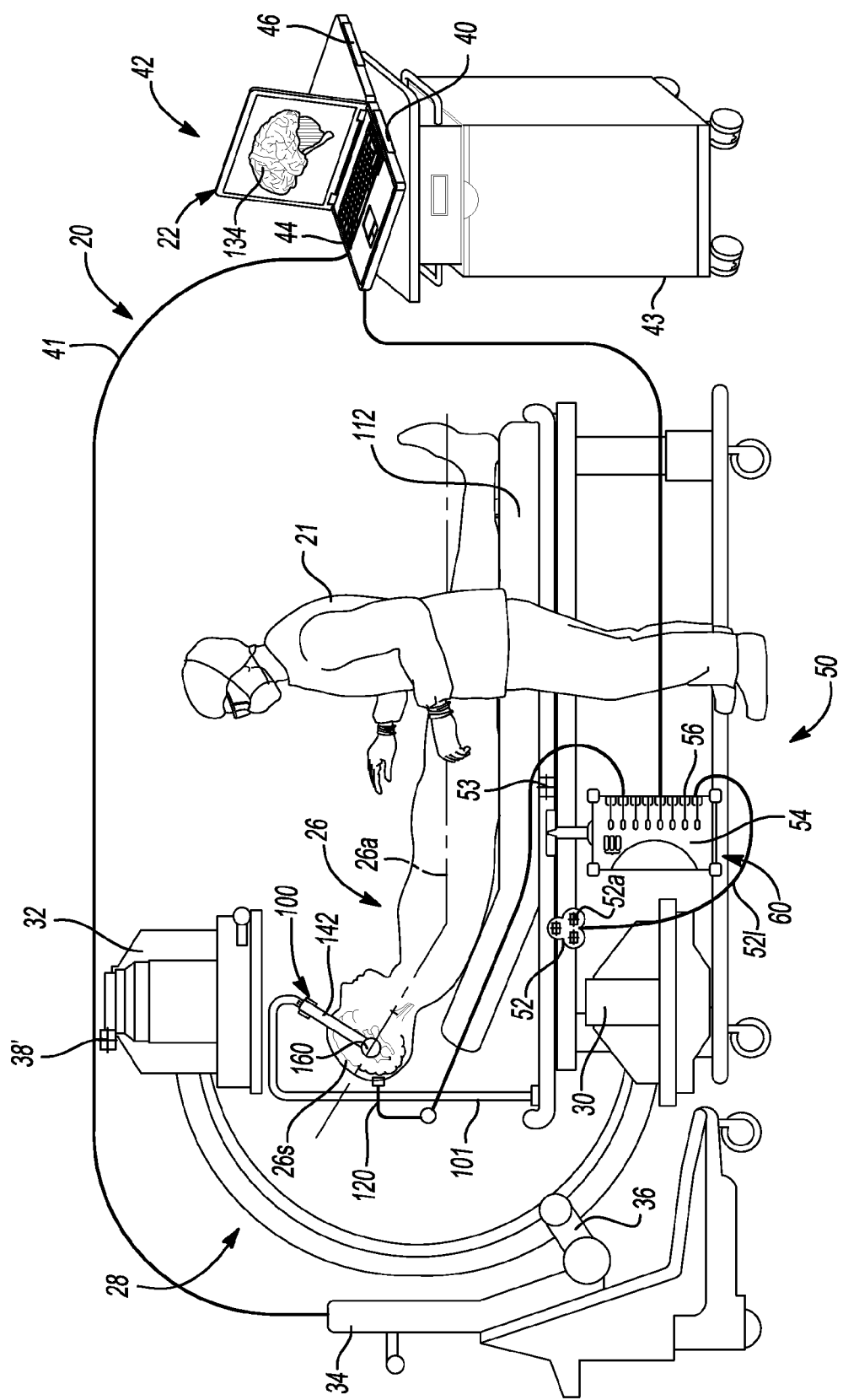
FIG. 1 is an environmental view of an operating room having a tracking system according to various embodiments.

Example embodiments will now be described more fully with reference to the accompanying drawings.

The following description is merely exemplary in nature and is not intended to limit the present disclosure, application, or uses. It should be understood that throughout the drawings, corresponding reference numerals indicate like or corresponding parts and features.

The present disclosure specifically provides an example of performing a procedure on a subject, such as a human patient. It is understood, however, that the subject invention is not limited to performing a patient. For example, a procedure can be performed on an animal subject as well. As a further alternative, the subject disclosure disclosing a device and a method can be performed relative to any appropriate volume. For example, a procedure can be performed relative to a volume, relative to a mechanical device or enclosed structure. The volume need not be of a living subject, but can be rather of an inanimate or animate object. In various examples the subject can be an object including an enclosed mechanical device. In various further examples, the subject can be a non-human animal A guided procedure can be performed with a navigation system 20, in FIG. 1. The guided procedure can be any appropriate procedure, such as a neural procedure, a spinal procedure, head (e.g. sinus) procedures, and an orthopedic procedure. The navigation system 20 can include various components, as will be discussed further herein. The navigation system 20 can allow a user, such as a surgeon 21, to view on a display 22 a relative position of an instrument 24 (illustrated in FIG. 2) to a coordinate system. The position that is tracked can include a location in space and an orientation of the tracked device in space. The coordinate system can be made relative to an image, such as in an image guided procedure, or can be registered to a subject 26 only, such as in an imageless procedure. As noted above, the subject can be a human patient or any other appropriate subject.

Briefly, an imageless system can be provided which allows registration of an instrument to subject space alone, rather than image space. In an imageless system, image data of the subject 26 need not be acquired at any time. Although image data can be acquired to confirm various locations of instruments or anatomical portions, such image data is not required. Further, the imageless system can be provided to allow for tracking the subject 26 and an instrument relative to the subject 26.

In an exemplary imageless system, a determination of a position of an anatomical structure can be made relative to the instrument and the locations of each can be tracked. For example, a plane of an acetabulum can be determined by touching several points with a tracked instrument. A position of a femur can be determined in a like manner. The position of the relative portions, including the instrument and the anatomical portion, can be displayed on a display, with icons or graphics. The display, however, need not include image data acquired of the patient. One skilled in the art will understand that other data can be provided in an imageless system, however, like atlas data or morphed atlas data. The atlas data can be image data that is generated or generalized from a subject. For example, a brain atlas can be generated based on detail analysis and study of image data of a brain of a selected patient. Nevertheless, an imageless system is merely exemplary and various types of imageless or image based systems can be used, including the image based system discussed below.

It should further be noted that the navigation system 20 can be used to navigate or track instruments including: catheters, probes, needles, guidewires, instruments, implants, deep brain stimulators, electrical leads, etc. Moreover, the instrument can be used in any region of the body. The navigation system 20 and the various instruments 24 can be used in any appropriate procedure, such as one that is generally minimally invasive, arthroscopic, percutaneous, stereotactic, or an open procedure. Although an exemplary navigation system 20 can include an imaging device 28, one skilled in the art will understand that the discussion of the imaging device 28 is merely for clarity of the present discussion and any appropriate imaging system, navigation system, patient specific data, and non-patient specific data can be used. Image data can be captured or obtained at any appropriate time with any appropriate device.

The navigation system 20 can include the optional imaging device 28. The optional imaging device 28 or any appropriate imaging device can be used to acquire pre-, intra-, or post-operative or real-time image data of a patient 26. The illustrated imaging device 28 can be, for example, a fluoroscopic x-ray imaging device that may be configured as a C-arm 28 having an x-ray source 30 and an x-ray receiving section 32. Other imaging devices may be provided and reference herein to the C-arm 28 is not intended to limit the type of imaging device. An optional calibration and tracking target and optional radiation sensors can be provided, as understood by one skilled in the art. Image data may also be acquired using other imaging devices, such as those discussed herein. An example of a fluoroscopic C-arm x-ray device that may be used as the optional imaging device 28 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, O-Arm® imaging system, etc.

An optional imaging device controller 34 can control the imaging device 28 to capture the x-ray images received at the receiving section 32 and store the images for later use. The controller 34 may also be separate from the C-arm 28 and/or control the rotation of the C-arm 28. For example, the C-arm 28 can move in the direction of arrow 28a or rotate about a longitudinal axis 26a of the patient 26, allowing anterior or lateral views of the patient 26 to be imaged. Each of these movements involves rotation about a mechanical axis 36 of the C-arm 28.

The operation of the C-arm 28 is understood by one skilled in the art. Briefly, x-rays can be emitted from the x-ray section 30 and received at the receiving section 32. The receiving section 32 can include a camera that can create the image data from the received x-rays. It will be understood that image data can be created or captured with any appropriate imaging device, such as a magnetic resonance imaging system, a positron emission tomography system, or any appropriate system. It will be further understood that various imaging systems can be calibrated according to various known techniques. Further, an imager tracking device 38' can be provided to track a position of the receiving section 32 of the imaging device 28 at any appropriate time by the navigation system 20.

The image data can then be forwarded from the C-arm controller 34 to a navigation computer and/or processor 40 via a communication system 41. The navigation processor 40 can include a processor that is configured to operate to navigate a procedure, including a general purpose processor or computer executing instructions for navigation. The communication system 41 can be wireless, wired, a hardware data transfer device (e.g. a physical-ROM and/or rewritable flash memory), or any appropriate system. A work station 42 can include the navigation processor 40, the display 22, a user interface 44, and an accessible memory system 46. It will also be understood that the image data is not necessarily first retained in the controller 34, but may be directly transmitted to the workstation 42 or to a tracking system 50, as discussed herein. The workstation 42 can be any appropriate system such as a substantially portable computer and/or processor system with an integrated display 22. The workstation 42 may include a substantially portable computer, such as known laptop or tablet computer configurations, further including ruggedized laptop computer configurations.

The work station 42 provides facilities for displaying the image data as an image on the displays 22, saving, digitally manipulating, or printing a hard copy image of the of the received image data. The user interface 44, which may be a keyboard, mouse, touch pen, touch screen, or other suitable device, allows the user 21 to provide inputs to control the imaging device 28, via the C-arm controller 34, or adjust the display settings of the display 22. The work station 42 can also be used to control and receive data from a coil array controller (CAC)/navigation probe or device interface (NDI) 54/56.

While the optional imaging device 28 is shown in FIG. 1, any other alternative 2D or 3D imaging modality may also be used. For example, any 2D 3D imaging device, including one that can collect images in time, such as isocentric fluoroscopy, bi-plane fluoroscopy, ultrasound, computed tomography (CT), multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative CT, single photo emission computed tomography (SPECT), or planar gamma scintigraphy (PGS) may also be used to acquire 2D or 3D pre- or post-operative and/or real-time images or image data of the patient 28. The images may also be obtained and displayed in two or three dimensions and in time. In more advanced forms, surface rendering regions of the body may also be achieved by incorporating patient data or other data from an atlas or anatomical model map or from pre-operative image data captured by MRI, CT, or echocardiography modalities and displaying it in time. A more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, can also provide functional image data superimposed onto anatomical data to be used to confidently reach target sites within the patient 26. It should further be noted that the optional imaging device 28, as shown in FIG. 1, provides a virtual bi-plane image using a single-head C-arm fluoroscope as the optional imaging device 28 by simply rotating the C-arm 28 about at least two planes, which could be orthogonal planes to generate two-dimensional images that can be converted to three-dimensional volumetric images. By acquiring images in more than one plane, an icon representing the location of an impacter, stylet, reamer driver, taps, drill, deep brain stimulators, electrical leads, needles, implants, probes, or other instrument, introduced and advanced in the patient 26, may be superimposed in more than one view on the display 22 allowing simulated bi-plane or even multi-plane views, including two and three-dimensional views.

With continuing reference to FIG. 1, the navigation system 20 can further include the tracking system 50 that includes a localizer 52, (e.g. which can also be referred to as a transmitter array, a tracking array, tracking coils, or coil array and can include a transmitter and/or receiver coil array). One skilled in the art will understand that the coil array 52 can transmit or receive and reference to a transmit coil array herein is merely exemplary and not limiting. The tracking system 50 can further include a coil array controller 54 that can have at least one navigation interface or navigation device interface 56 for connection of the localizer 52, an instrument tracking device, and a dynamic reference frame 58. The coil array controller 54 and the at least one navigation interface 56 can be provided in a single substantially small CAC/NDI container 60.

Figure 2:
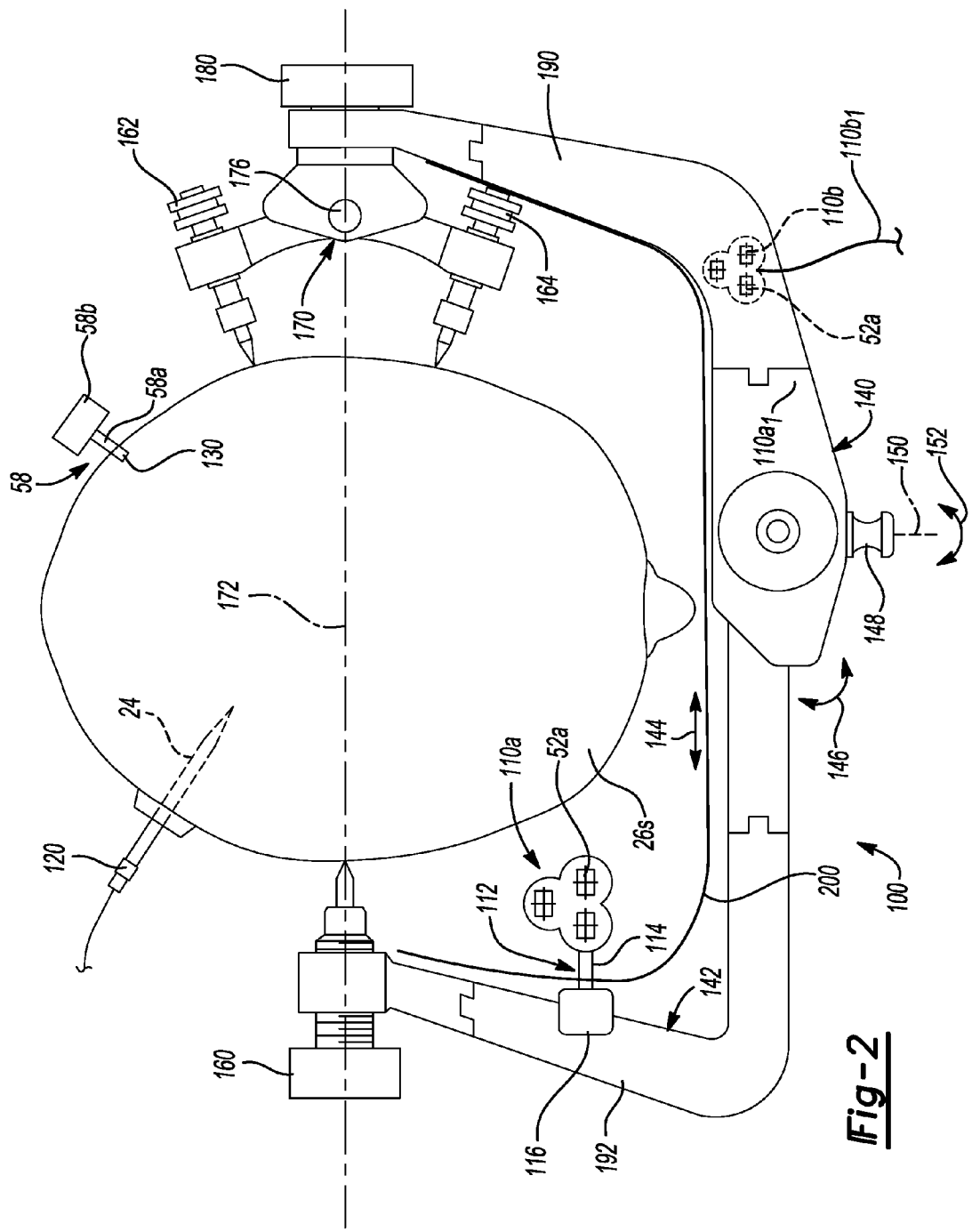
FIG. 2 is a view of a head holder having a localizer associated therewith.

With continuing reference to FIG. 1 and additional reference to FIG. 2, the dynamic reference frame 58 can include a dynamic reference frame member 58a and a removable tracking device 58b. Alternatively, the dynamic reference frame 58 can include the tracking device 58b that is formed integrally with the dynamic reference frame member 58a. For example, the tracking device 58b can be connected directly to the patient 26, including a skull 26s of the patient 26 or a head-holder 100. The head holder 100 can be a head holder such as the MAYFIELD® Composite Series Skull Clamp including those sold by Integra LifeSciences Corporation having a place of business at Plainsboro, N.J., USA. The head holder 100 can be held with a member 101 to the bed 112 or any other selected element to hold the patient 26. One skilled in the art will understand that the tracking device 58b can be any appropriate device and can be an emitter, a receiver, a reflector, a sensor to sense a field, or any other appropriate device that can be tracked by a tracking system including a localizer. Also the tracking device 58b can be wired to the other portions of the system 20 or have a wireless communication therewith, as discussed herein.

The first localizer 52 can include that described in U.S. patent application Ser. No. 10/941,782, filed Sep. 15, 2004, now U.S. Pat. App. Pub. No. 2005/0085720, and entitled "METHOD AND APPARATUS FOR SURGICAL NAVIGATION", herein incorporated by reference. The first localizer may also be supplemented and/or replaced with a second localizer 110a and/or a third localizer 110b. As is understood the localizer array, according to any of the various embodiments, can transmit signals that are received by the dynamic reference frame 58, and a tracking device 120 that is associated with (e.g. connected to) the instrument. The dynamic reference frame 58 and the tracking device 120 can then transmit signals based upon the received/sensed signals of the generated fields from one or more of the localizers 52, 110a, and/or 110b.

It should further be noted that the entire tracking system 50 or parts of the tracking system 50 may be incorporated into other portions in the operating theatre. Incorporating and/or integrating the tracking system 50, or at least portions thereof, may provide an integrated system. The integrated system can provide for various features such as known or reduced field interference or distortion.

For example, one of the localizers, or any appropriate or selected portion of the tracking system 50, can be incorporated into the imaging device 28. The transmitter coil array 52 can be attached to the receiving section 32 of the C-arm 28. It should be noted, however, that the transmitter coil array 52 may also be positioned at any other location as well. For example, the transmitter coil array 52 may be positioned at the x-ray source 30.

As a further example, one or more of the localizers 110a, 110b can be incorporated into the head holder 100, as illustrated in FIG. 2 and discussed further herein. In one example the localizer 110 can be connected to a portion of the head holder 100 with a clamp system 112. The clamp system 112 can include an extending member 114 and a closable claw portion 116. In yet a further example, the localizer 110b can be formed as and/or within a portion of the head holder 100, such as molded therewith. Also, the localizer can be positioned within or atop an operating room (OR) table 120 positioned below the patient 26, on siderails associated with the OR table 120, or positioned on the patient 26 in proximity to the region being navigated, such as on the patient's chest.

The localizer, according to various embodiments, can include a coil array 52a that is used in an electromagnetic tracking system. The localizer 52 (although localizer 52 may be discussed as an example herein, it is understood that any of the localizers 52, 110a, 110b can include the discussed features) may also be positioned in the items being navigated, further discussed herein, including the instrument 24. Also, the coil array 52a of the localizer 52 can include a plurality of coils that are each operable to generate distinct electromagnetic fields into the navigation region of the patient 26, which is sometimes referred to as patient space. Electromagnetic systems are generally described in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The coil array 52a is controlled or driven by the coil array controller (CAC) 54. The CAC 54 can transmit a signal with a transmission line 52l, 110al, and 110bl to the respective localizers 52, 110a, 110b. The coil array 52a of each localizer 52, 110a, 110b can have more than one coil that is driven by the coil array controller 54 in a time division multiplex, a frequency division multiplex manner, or selected appropriate manner. Each coil array 52a can include an array of coils provided to generate a selected field. For example, at least three substantially orthogonal coils may generate three substantially orthogonal fields. In this regard, each coil of the coil array 52a may be driven separately at a distinct time or all of the coils may be driven simultaneously with each being driven by a different frequency, as discussed further herein. It is understood, however, that any selected number of coils can generate a diverse field that can be resolved for tracking a tracking device. Also, individual coils can be driven at more than one frequency simultaneously.

Upon driving the coils in the coil array 52a with the coil array controller 54, electromagnetic fields are generated within the patient 26 in the area where the medical procedure is being performed, which is again sometimes referred to as patient space. The electromagnetic fields generated in the patient space induce currents in the tracking devices 62, 94 positioned on or in the instruments 24. These induced signals from the instrument 24 are delivered to the navigation device interface 56 and can be forwarded to the coil array controller 54. The navigation probe interface 56 may provide all the necessary electrical isolation for the navigation system 20, as discussed herein. The navigation device interface (NDI) 56 can also include amplifiers, filters and buffers to directly interface with the tracking devices 58b, 120. Alternatively, the tracking devices 58b, 120, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled with a physical transmission line to the NDI 56.

When the navigation system 20 uses an EM based tracking system, various portions of the navigation system 20, such as tracking devices 58b, 120 are equipped with at least one, and generally more coils that are operable with the EM localizer arrays 52, 110a, 110b. Alternatively, the tracking system may be a hybrid system that includes components from various tracking systems such as optical, acoustic, etc.

The EM tracking device 120 on the instrument 24 can be in a handle or inserter that interconnects with an attachment and may assist in placing an implant or in driving a portion. The instrument 24 can include a graspable or manipulable portion at a proximal end and the tracking sensor device that can be fixed near the manipulable portion of the instrument 24 or at a distal working end, as discussed herein. The tracking device 24 can include an electromagnetic sensor to sense the electromagnetic field generated by the localizer 52, 110a, 110b that can induce a current in the tracking device 120.

The dynamic reference frame (DRF) 58 of the tracking system 50 can also be coupled to the NDI 56 to forward the information to the CAC 54 and/or directly to the processor 40. The DRF 58, according to various embodiments, may include a magnetic and/or electromagnetic field detector as the tracking device 58b. The dynamic reference frame 58 may be fixed to the patient 26 adjacent to the region where navigation is occurring so that any movement of the patient 26 is detected as relative motion between the localizer 52 and the dynamic reference frame 58. The dynamic reference frame 58 can be interconnected with the patient 26 in any appropriate manner, including those discussed herein. Any relative motion is forwarded to the coil array controller 54, which updates registration correlation and maintains accurate navigation, further discussed herein. If the dynamic reference frame 58 is electromagnetic it can be configured as a pair or trio of substantially mutually orthogonally oriented coils, each having the same center or may be configured in any other non-coaxial or co-axial coil configurations.

The dynamic reference frame 58 may be affixed externally to the patient 26, adjacent to the region of navigation, such as on the patient's skull 26s, etc., as shown in FIG. 2. The dynamic reference frame 58 can be affixed to the patient's skin, by way of a selected adhesive patch and/or a tensioning system. The dynamic reference frame 58 may also be removably attachable to a fiducial marker 130. The fiducial markers can be anatomical landmarks or members attached or positioned on the patient's 26 body. The dynamic reference frame 58 can be connected to a bone portion of the anatomy, such as the skull 26s. The bone portion can be adjacent, the area of the procedure, the bone of the procedure, or any appropriate bone portion.

Briefly, the navigation system 20 operates as follows. The navigation system 20 creates a map between all points in the image data or image space and the corresponding points in the patient's anatomy in patient space. After this map is established, the image space and patient space are registered. In other words, registration is the process of determining how to correlate a position (i.e. a location and orientation) in image space with a corresponding point in real or patient space. This can also be used to illustrate a position of the instrument 24 relative to the proposed trajectory and/or the determined anatomical target. The work station 42 either alone or in combination with the coil array controller 54 and/or the C-arm controller 34 identify the corresponding point on the pre-acquired image or atlas model relative to the tracked instrument 24 and display the position on display 22 and relative to an image 134 that is based on or generated with acquired or accessed image data. Each of the systems described above may also be incorporated into a single system or executed by a single processor. This identification is known as navigation or localization. An icon representing the localized point or instruments is shown on the display 22 within several two-dimensional image planes, as well as on three dimensional images and models and any of these shown in time. Also, the shown points, instruments, and/or icons can be based on models of the various items and points.

To register the patient 26 to the image 134, the user 21 may use point registration by selecting and storing particular points from the pre-acquired images and then touching the corresponding points on the patient's anatomy with a pointer probe or any appropriate tracked device, such as the instrument 24. The navigation system 20 analyzes the relationship between the two sets of points that are selected and computes a match, which allows for a determination of a correlation of every point in the image data or image space with its corresponding point on the patient's anatomy or the patient space.

The points that are selected to perform registration or form a map are the fiducial markers 134, such as anatomical or artificial landmarks. Again, the fiducial markers 134 are identifiable on the images and identifiable and accessible on the patient 26. The fiducial markers 134 can be artificial landmarks that are positioned on the patient 26 or anatomical landmarks that can be easily identified in the image data. The artificial fiducial markers 134, can also form part of the dynamic reference frame 58, such as those disclosed in U.S. Pat. No. 6,381,485, entitled "Registration of Human Anatomy Integrated for Electromagnetic Localization," issued Apr. 30, 2002, herein incorporated by reference. It will be understood that any appropriate number of the fiducial markers 134 can be provided with and/or separate from the DRF 58.

The navigation system 20 may also perform registration using anatomic surface information or path information as is known in the art (and may be referred to as auto-registration). The navigation system 20 may also perform 2D to 3D registration by utilizing the acquired 2D images to register 3D volume images by use of contour algorithms, point algorithms or density comparison algorithms, as is known in the art. An exemplary 2D to 3D registration procedure is set forth in U.S. Ser. No. 10/644,680, filed on Aug. 20, 2003, now U.S. Pat. App. Pub. No. 2004-0215071, entitled "Method and Apparatus for Performing 2D to 3D Registration", hereby incorporated by reference.

In order to maintain registration accuracy, the navigation system 20 continuously can track the position of the patient 26 during registration and navigation with the dynamic reference frame 58. This is because the patient 26, dynamic reference frame 58, and localizer 52 may all move during the procedure, even when this movement is not desired. Alternatively the patient 26 may be held immobile once the registration has occurred, such as with the head holder 100. Therefore, if the navigation system 20 did not track the position of the patient 26 or area of the anatomy, any patient movement after image acquisition would result in inaccurate navigation within that image. The dynamic reference frame 58 allows the tracking system 50 to track the anatomy and can assist in registration. Because the dynamic reference frame 58 is rigidly fixed to the patient 26, any movement of the anatomy or the transmitter coil array 52 is detected as the relative motion between the transmitter coil array 52 and the dynamic reference frame 58. This relative motion is communicated to the coil array controller 54, via the navigation probe interface 56, which updates the registration correlation to thereby maintain accurate navigation.

The dynamic reference frame 58 can be affixed to any appropriate portion of the patient 26, and can be used to register the patient to the image data, as discussed above. For example, when a procedure is being performed relative to the skull or cranium 26s, the dynamic reference frame 58 can be interconnected with the cranium 26s. The dynamic reference frame 58 can be interconnected with the cranium 26s in any appropriate manner, such as those discussed herein according to various embodiments.

Navigation can be assisted with registration and the navigation system 20 can detect both the position of the patient's anatomy and the position of the tracking device 120 attached to the instrument 24. Knowing the location of these two items allows the navigation system 20 to compute and display the position of the instrument 24 or any portion thereof in relation to the patient 26. The tracking system 50 is employed to track the instrument 24 and the patient 26 simultaneously.

The tracking system 50, if it is using an electromagnetic tracking assembly, can work by positioning the localizer 52, 110a, 110b adjacent to the patient space to generate an electromagnetic (EM) field, which can be low energy and also generally referred to as a navigation field. Because every point in the navigation field or patient space is associated with a unique field strengths and directions, the electromagnetic tracking system 50 can determine the position of the instrument 24 by measuring the field strengths, directions, and/or components thereof at the tracking device 120 location. The dynamic reference frame 58 is fixed to the patient 26 to identify the position of the patient 26 in the navigation field. The electromagnetic tracking system 50 continuously recomputes the relative position (including location and orientation) of the dynamic reference frame 58 and the instrument 24 during localization and relates this spatial information to patient registration data to enable image guidance of the instrument 24 within and/or relative to the patient 26. In various embodiments, as discussed herein, the localizer 110a, 110b is affixed to the head holder 100 which holds the skull 26s fixed relative to the localizer 110a, 110b. This may be able to allow for constant registration as the skull 26s is held immobile relative to the localizer 110a, 110b that generates the EM navigation field.

To obtain a maximum accuracy it can be selected to fix the dynamic reference frame 58 in each of at least 6 degrees of freedom. Thus, the dynamic reference frame 58 or any tracking device, such as the tracking device 120, can be fixed relative to axial motion X, translational motion Y, rotational motion Z, yaw, pitch, and roll relative to the portion of the patient 26 to which it is attached. Any appropriate coordinate system can be used to describe the various degrees of freedom. Fixing the dynamic reference frame relative to the patient 26 in this manner can assist in maintaining maximum accuracy of the navigation system 20.

The instrument 24 can be any appropriate instrument (e.g., a catheter, a probe, a guide, etc.) and can be used for various mechanisms and methods, such as delivering a material to a selected portion of the patient 26, such as within the cranium 26s. The material can be any appropriate material such as a bioactive material, a pharmacological material, a contrast agent, or any appropriate material. As discussed further herein, the instrument 24 can be precisely positioned via the navigation system 20 and otherwise used to achieve a protocol for positioning the material relative to the patient 26 in any appropriate manner, such as within the cranium 26s. The instrument 24 may also include a brain probe to perform deep brain stimulation.

As illustrated in FIG. 2, the head holder 100 can be provided with a plurality of moveable and configurable portions including a first or main arm 140 and a second or supplemental arm 142. The head holder 100 is an example of any possible configurable theater system. Generally, a configurable theater system can be a system that is able to be selectively (i.e. changeably) configured or deformed prior to or during a procedure. Thus, the configurable theater system may not always be in the same configuration between two different procedures. Different configurations of the configurable theater system can distort the field generated from the localizer 110*a*, 110*b* in different ways to generate a distorted generated field that becomes or is used as the navigation field during a procedure using the configurable theater system. Selected configurable theater systems can include those disclosed in U.S. Pat. App. Pub. NO. 2004/0199072, published Oct. 7, 2004; U.S. Pat. No. 8,301,226; and U.S. Pat. No. 7,313,430; all incorporated herein by reference.

The two arms 140 and 142 of the head holder can be designed or manufactured to move relative to one another in selected ways. For example, the two arms 140, 142 may be provided to move relative to one another in both a linear direction 144 and in rotational or angular directions 146. It is understood, however, that the arms 140, 142 may be limited or immoveable in a selected direction. Other movements between the two arms 140 and 142 can also be allowed, particularly relative to the patient's skull 26*s* via rotation around a mounting pin or holder 148 where the head holder 100 can rotate around a long axis 150 of the mounting pin 148 generally in the direction of arrow 152. The head holder 100 can be the clamp as discussed above, such a clamp is generally known in the art and will not be described in detail here other than for the features related to the navigation system. Accordingly, the head holder 100 can further include a main holding pin 160 that can be driven to at least contact and possibly penetrate a distance into the skull 26*s*. Two additional head holder pins 162 and 164 can also be driven into contact or penetration with the skull 26*s*. The two additional pins 162, 164 can be interconnected with a rotational arm 170 that can move in at least one, and generally at least two, degrees of freedom including rotation around an axis 172 and pivoting along or around an axis 176 that is substantially orthogonal to the axis 172. A locking mechanism can include a threaded locking mechanism with a knurled handle 180 to lock the movement arm 170 in a selected orientation relative to the first arm 140.

Accordingly, the head holder 100 can be positioned at various and numerous orientations relative to the skull 26*s*. Each of the numerous configurations can induce or cause distortions into the electromagnetic field that is generated by the localizer 110*a* and/or 110*b*. The discussion herein will exemplarily relate to the localizer 110*a*, but it is understood that similar considerations can be made for the second localizer 110*b*. Additionally, it is understood that the first and second localizer 110*a* and 110*b* need not be used together and/or simultaneously with the head holder 100. Moreover, localizers can be interconnected with the second arm 142 or other appropriate portions of the head holder 100.

The head holder 100 and the various configurations can affect the magnetic field generated by the localizer 100*a* by inducing distortions therein due to the materials of the head holder 100. The distorted field will then become the navigation field that is used to track the location of tracking devices, such as the tracking device 58*b*, within the navigation field and the subject space. Thus, the navigation field may not be the ideal field that is theoretically generated by the localizer 100*a*.

Distortions can occur because the head holder 100 can be formed of a metal, such as a conductive metal, which can interact with the EM field generated by the localizer 110*a* to generate distortions therein, such as generally due to eddy currents. As is understood by one skilled in the art, eddy currents can be induced in a conductive material by the generated fields from the localizer 110*a*. The eddy currents can generate fields that distort the generated field from the localizer 110*a*. The distortions, e.g. from the eddy currents, can affect the electromagnetic field sensed by the tracking devices 58*b* and/or 120 when determining a location of the tracking devices. Again, the discussion herein will be related to the tracking device 120 interconnected with the instrument 24, but is understood that the relevant discussion can relate to any appropriate tracking devices associated with the patient 26. Moreover, the tracking device 120 can be placed at a distal tip of the instrument 24 and be inside the skull 26*s*.

As discussed above, the induced current in the tracking device 120, based upon the sensed field generated by the localizer 110*a*, allows for a determination of the position of the tracking device 120 relative to the localizer 100*a*, the patient 26, and/or the tracking device 58*b*. Once the patient 26 is registered to the image 134, tracking the tracking device 120 can allow for illustration of the instrument 24 relative to the image 134 of the patient 26. Accordingly, distortion of the EM field generated by the localizer 110*a* can affect accuracy and appropriately identifying a location of the instrument 24.

Initially, it is understood that the head holder 100 substantially fixes the skull 26*s* relative to the portions of the head holder 100. The localizer 100*a* is also fixed relative to the portions of the head holder 100. Accordingly, tracking the DRF 58 relative to the localizer 100 for determining a relative location of the instrument 24, including the tracking device 120 associated therewith, may be unnecessary. By fixing the localizer 100*a* to the head holder 100, which is subsequently fixed to the skull 26*s*, then navigating an instrument within the volume of the skull 26*s* need not require an additional immovable dynamic reference frame to determine the location of the skull 26*s*. Because the skull 26*s* is immoveable relative to the localizer 100*a*, based upon the fixation point of the head holder 100. Accordingly, by integrating or fixedly attaching the localizer 100*a* to the head holder 100, the need for additional fixation of the DRF 58 to the skull 26*s* can be eliminated. As is understood in the art, the DRF 58 can generally be driven into skull 26*s* to assure appropriate fixation. Accordingly, eliminating the DRF 58 can eliminate possible trauma to the patient 26.

The head holder 100 can also be formulated, such as through design, material selection, and the like to substantially reduce and/or eliminate distortion of the EM field generated with a localizer 100*a*. The parts that would not substantially affect the EM field can be referred to as non-distorting parts. Generally, a non-distorting part can be a part that has low conductivity, such as less than 10% as conductive as copper metal, and low susceptibility to magnetic fields, such as less than 10% magnetic susceptibility. Thus, a non-distorting part will generally have low conductivity and low magnetic permeability. It can also refer to a part that will distort a field no more than that can be calculated for to allow a determination of a location of a tracked device within the distorted field.

In various examples, the materials for various parts of the arms 140, 142 can be formed of non-conductive materials, such as polymers, including substantially rigid polymers that can withstand the forces applied by the head holder 100 relative to the skull 26*s*. For example, the part of the arm 140 near where the localizer 110*a* is connected can be formed of non-conductive material. The non-conductive material can form a non-distorting part 190 of the arm 140. Similarly, a part of the second arm 142 that is near the skull 26*s*, including particularly the region where the instrument 24 is inserted into the skull 26*s*, can also be formed of a non-conductive and/or non-distorting material to form a second non-distorting region 192. The non-distorting or less distorting parts 190, 192 can be positioned relative to the patient 26 to attempt to substantially minimize distortion of the field that is generated by the localizer 110a. The material selected for the non-distorting parts 190, 192 can be selected to be substantially non-conductive or non-ferromagnetic material, such as those generally understood by one skilled in the art. Examples include non-conductive polymers, non-conductive ceramics, and insulated materials (e.g., insulated conductive materials). The non-distorting parts 190, 192 generally will reduce or eliminate eddy currents from being formed therein.

Additionally, the design of the coil array 52a within the localizer 110a can also be maximized to minimize distortion based upon interaction of the EM field generated by the localizer 110a when interacting with the head holder 100. The size and/or position of the coil array 52a within the localizer 110a can also be positioned and designed to minimize the distortions, such as positioning the coil array 52a at a position relative to the regions that are outside of the non-distorting parts 190. Additionally, the physical design of the head holder 100 can be altered and/or calibrated to minimize distortion of the EM field generated by the localizer 110a. For example, the arms 140 and 142 can be angled relative to the position of the localizer 110a such that they are extending away from the localizer 110a and the localizer 110a can be positioned substantially adjacent or near the skull 26s.

In addition, various electromagnetic shielding can be positioned relative to the head holder or between the head holder 100 and the localizer 110a. As discussed above, the material in the non-distorting part 190 can be shielded conductive material. Similarly, shielding can be positioned around portions of the head holder 100 to substantially eliminate the distortion of the head holder 100 of the field generated by the localizer 110a. For example, a magnetic but non-conductive shield 200 can be positioned between the head holder 100 and the patient 26 that is mounted or interconnected with the spindle pin 148. The shield 200 can be connected to the head holder 100 such that the EM field generated by the localizer 110a is substantially directed towards the patient's skull 26s while being shielded from the majority of the interfering head holder 100. By positioning the localizer 110a between the shield 200 and the subject skull 26s, where the head holder 100 is substantially positioned on an exterior or opposite side of the shield 200, can substantially eliminate or reduce distortion of the head holder 100 on the EM field generated by the localizer 110a.

Accordingly, the head holder 100 can be designed to be shaped, shielded, and formed of selected materials to reduce distortion of an EM field generated by the localizer 110a. As discussed above, various non-distorting parts 190 of the head holder 100 can be designed to be formed of non-conductive or non-ferromagnetic materials to reduce distortion of an EM field generated by the localizer 110a. Moreover, the physical design and configuration of the head holder 100 can be such that the localizer 110a is positioned away from distorting portions of the head holder 100. Also, the shield 200 can be positioned relative to the head holder 100, the patient skull 26s, and the localizer 110a to eliminate or reduce distortion of the EM field generated by the localizer 110a relative to the skull 26s. In particular, the shield 200 can be placed to reduce or eliminate field distortion at the location of the instrument 24 and the associated tracking device 120.

In addition to the design and selection of materials for the head holder 100, during manufacturing and assembly of the head holder, such as any factory calibration, the localizer 110a can be calibrated relative to the head holder 100. For example, the tolerances and assembly of the head holder 100 can be held to substantially precise and tight to ensure that any distortion generated by the head holder 100 is substantially consistent between different head holder assemblies. For example, the difference in size and shape between different configured theater systems can be about 1 millimeter (mm) to about 20 centimeters (cm). Additionally, various portions of the head holder 100 can vary by about 1 degree to about 180 degrees relative to one another in different configurations.

Figure 3A:
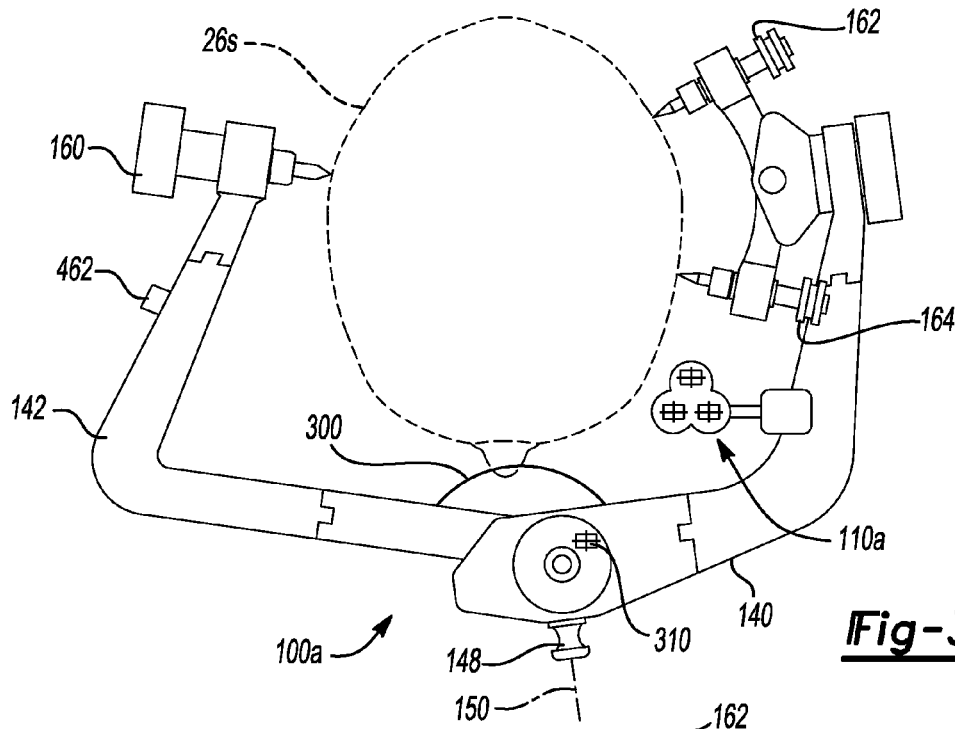
FIG. 3A is a first configuration of a head holder, according to various embodiments.
Figure 3B:
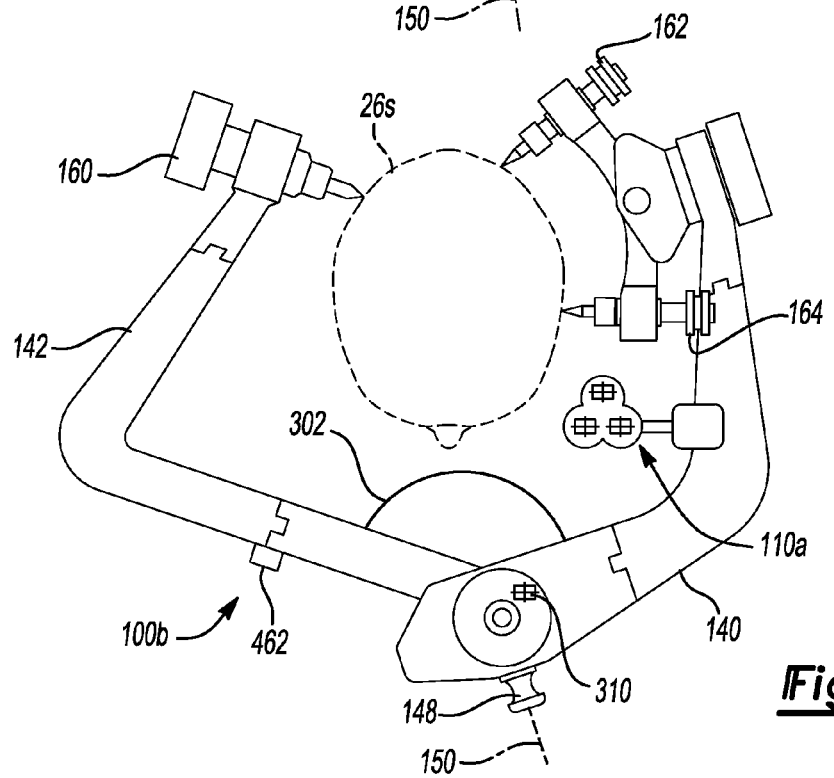
FIG. 3B is a second configuration of the head holder, according to various embodiments.

The head holder 100 can be configured in various different configurations, as illustrated in FIGS. 3A and 3. The head holder 100 can include a first configuration 100a, illustrated in FIG. 3A, and a second head holder configuration 100b, illustrated in FIG. 3B. In the head holder configuration illustrated 100a, an angle 300 can be formed between the first arm 140 and the second arm 142 relative to the axis 150 along the holding post 148. The angle 300 can be any appropriate angle, such as about 170 degrees between the first arm 140 and the second arm 142. The configuration of the first arm 140 relative to the second arm 142 can impose specific distortions on a field generated by the localizer 110a. The specific configuration of the head holder 100 including the angle 300 between the first arm 140 and the second arm 142 can be used to measure and determine the distortion in the field generated by the EM localizer 110a.

The known distortion can then be modeled, and/or saved, to a database stored in the memory system 46 for access by the processor system 40 or a user at a selected time. The distorted field can include distorted field parameters that define the navigation field. The distortion based upon the configuration including the angle 300 can be known and substantially the same when the manufacturing of the head holder 100 is substantially precisely controlled including the design, tolerances, and selected materials. Accordingly, the distorted field parameters when the configuration of the head holder 100 includes angle 300 can be known and used to determine the navigation field that is the distorted field generated by the localizer 110a at any time that the angle 300 is formed between the first arm 140 and the second arm 142. It is understood, however, that other portions of the head holder can be configured differently relative to the arms 140, 142 including the head holding pins 160, 162 and 164. Accordingly, it is understood that configurations of these can also be substantially precisely determined and a distortion effect on the EM field can be determined.

As an example of a different configuration, as illustrated in FIG. 3B, the first arm 140 can also be positioned at a second angle 302 relative to the second arm 142. The second angle 302 can be any appropriate angle that can be different than the first angle 300, including about 160 degrees. Again, the distortion due to the orientation of the first arm 140 and the second arm 142 at the angle 302 that affects the field or distorts the field generated by the localizer 110a can be precisely determined and measured and saved in the memory system 46 for later retrieval, such as by the processor system 40. The distortion when the head holder 100 is at the configuration 100b where the angle 302 is produced can be substantially precisely determined during use after a factory or assembly calibration. Accordingly, determination of the distortion of the EM field generated by the localizer 100a need not be determined each time that the head holder is reconfigured.

It is understood that the stored distorted field parameters can be based on calibration measurements of the distorted field during a calibration period. Where the measurements of the distorted field are taken at known three-dimensional locations relative to the head holder 100. For example, during manufacture of the head holder 100, or any appropriate configurable theater system, the localizer 110a can be positioned and the field generated. The distorted field can then be measured at a plurality of known physical locations relative to the head holder 100. The measured field strengths can be stored in the memory system 46 in a look-up table (or any appropriate data storage configuration) as the distorted field parameters when the head holder 100 is in a selected configuration. The field strengths can then be measured when the head holder is at all possible configurations and all of the measurements can be stored in the look up table. As discussed herein, a subset of all possible configurations can be made and fields measured and an interpolation between the subset can be used for determining a specific configuration and/or distortion. Following calibration, the head holder 100 can be configured during a procedure into a procedure configuration. The procedure configuration can be used to recall the appropriate field parameters from the look up table in the memory system 46 based on the calibration. It is understood that the recall can be substantially automatic by the processor 40 and need not include further user intervention for navigation other than entering the configuration or configuring the head holder 100. As discussed herein, sensors can be used to determine the configuration of the head holder 100. Further, maintaining tight tolerances between different head holders (e.g. serially) produced can eliminate the need to calibrate each head holder produced.

Various position sensors and measuring devices can be associated with the head holder 100 to determine when various configurations are reached or achieved. For example, an angle sensor 310, such as a potentiometer, can be positioned between the two arms 140 and 142 to measure an angle between the two arms 140 and 142. The angle sensed by the angle sensor 310 can be transmitted to the navigation system work station 42, as discussed above, and the angle determined can be used to retrieve the appropriate distorted field information from the lookup table in the memory system 46. The distorted field information can be used to determine the field strengths of the distorted field to be used as the navigation field within the patient space to allow for substantially precise navigation of the instrument 24 even though the field generated by the localizer 110a is distorted by the head holder 100. Because the distortion of the field by the head holder 100 is substantially known and precisely determined during factory calibration when the angle, or other appropriate and known changeable (i.e. configurable) configuration of the head holder 100 is determined, the appropriate distorted field information can be retrieved for use during navigation of the instrument 24. Thus, the determination of the distorted field for navigation need not include or require any user input regarding the configuration of the head holder 100. The user may simply configure the head holder 100 and the navigation can proceed once the processor 40 has retrieved the appropriate distorted field parameters due to the received position signal from the sensor 310.

As discussed above, the head holder 100 can include various design features and manufacturing techniques to assist in reducing, eliminating, or making consistent distortion in an EM field generated by the localizer 110a. The head holder 100, however, as discussed above, can be moved to various configurations as illustrated in FIGS. 3A and 3B. It is further understood that moveable portions of the head holder 100 can be moved in different manners during an operative procedure by a user, or person directed by the user, to ensure that a procedure occurs according to a plan or selected desired result. Moreover, it is understood that the localizer 110a can be interconnected with selected configurable devices other than the head holder 100. For example, the localizer 110a can be interconnected with the operating room bed 112, such as in a substantially fixed manner. The operating room bed 112 can also be moved into various configurations, as illustrated in FIG. 1 where the patient holding patient contacting portion is movable relative to a support member, during a use. Accordingly, it can be selected to include additional adaptive or active mechanisms to assist in limiting, eliminating, or determining distortion of an EM field generated by the localizer 110a during an operative procedure. Accordingly, it is understood that the head holder 100 is merely exemplary of possible configurable theater systems.

The work station 42, as discussed above, can include a processor for executing various instructions based on algorithms during an operative procedure when the localizer 110a is emitting a field for navigation of the instrument 24. It is understood, however, that additional or separate processors can be used to calculate or determine the distorted field based upon various algorithms discussed further herein.

The active or adaptive distortion compensation can include a process as illustrated in flowchart 400 in FIG. 4, which can be an algorithm to be executed by the processor of the work station 42 or any selected processor. The flowchart 400 can start at the start block 402. The method of flowchart 400 can then include configuring the head holder in block 404, including moving the head holder to a selected configuration, such as those illustrated in FIGS. 3A and 3B and then accessing/entering the configuration of the head holder in block 406. It is understood that configuring the head holder in block 404 is not a requirement of the flowchart, but is illustrated and discussed for clarity of the flowchart 400. Thus, physically configuring of the head holder 100 may not be a portion of the algorithm that is executed by the processor of the work station 42, but can be a physical act performed by a user. Accordingly, the flowchart 400 can include simply accessing or entering the configuration of the head holder in block 406 after beginning the flowchart in block 402. Accessing the configuration of the head holder 100 can include receiving a signal from the sensor 310 associated with the head holder 100 to determine the configuration of the head holder 100.

In accessing or entering the configuration of the head holder, the work station 42 can access or have entered therein the configuration of the head holder 100. As discussed above, the user 21 can move the head holder 100 into a selected configuration. The user can then use the user input 44 to input the configuration. For example, the user 21 can input the angle between the first arm 140 and the second arm 142 as a configuration of the head holder 100. Alternatively, or in combination therewith, the work station 42 can access the configuration of the head holder 100 by receiving a signal from the angle sensor 310 associated with the head holder 100 to determine the configuration of the head holder 100. As discussed above, it is understood that a plurality of sensors can be provided with the head holder 100 to ensure an appropriate determination of the configuration of the head holder 100. Accordingly, rotational and angle sensors can be positioned and formed onto the head holder 100 at a plurality of locations, including at each or between each moveable part of the head holder 100, to ensure an appropriate measurement of the exact configuration of the head holder 100.

After accessing or entering the configuration of the head holder in block 406, a determination of whether the access or entered configuration is identical to a saved configuration is made in block 410. As discussed above, as illustrated in FIGS. 3A and 3B, the configuration of the head holder 100 can be moveable to selected and known configurations. The known configurations can be determined and the effects on the field generated with the localizer 100*a* can be determined during a factory or pre-installation calibration. The factory calibration of the distorted field can be saved in the storage device 46, as discussed above. The stored information can include field parameters that indicate the field as distorted from a pure or undistorted field from the localizer 110*a* in a database, as discussed above, including in the form of a lookup table. Accordingly, each of the distorted fields can be related to a configuration of the head holder 100.

The accessing the database to determine whether the accessed or entered configuration from block 406 is identical to a saved one can therefore be determining whether the factory calibrated configuration is one that matches the actual configuration of the head holder 100 during the operative procedure. If it is determined that the accessed or entered configuration is identical to one saved in block 410, then the yes path through yes block 416 can be followed to recall the distorted field parameters from the database, e.g. lookup table, in the storage system 46 based upon a predetermined calibration in block 418. The distorted field can be one that is known or measured based upon the distortions of the field from the head holder 100. The distorted field can be the navigation field that is used to navigate the tracking device relative to the patient 26 or subject in the subject space, as is generally understood by one skilled in the art.

The recalled distorted field parameters can therefore allow for navigation within a distorted field that is distorted by the head holder 100 as long as the field is known in the volume of navigation space. The navigation space may, however, be limited due to areas where extensive distortion occurs and navigation is not possible. Regions or volumes where navigation is not possible to a determined preciseness (such as a navigation location error of less than about one millimeter) can be identified as no-navigation volumes. The no-navigation volumes can be those volumes that are either too distorted or not calibrated relative to the subject space of the patient. The no-navigation volumes can also be recalled in block 420. For a saved configuration, however, it is understood that the no-navigation volumes may be small compared at least to the navigable volumes.

The identified no-navigation volumes can be used by the navigation system 20 to provide feedback to the user 21 when an instrument is not in a navigable area or to stop navigation. Feedback can include an audible warning, a visual warning on the display device 22, or other appropriate feedback. Additionally, the navigation system 20 can stop navigation such as removing a display on the display device 22 so that the user is notified that a location of the instrument 24 is no longer being properly or accurately tracked by the navigation system 20.

Once the distorted field parameters are recalled, the procedure can then occur by navigating with the distorted field in block 430. As discussed above, the distorted field can be used to navigate the instrument 24 as long as the distorted field is distorted at known parameters within the navigation space. The procedure can then end in block 440. It is understood, however, that the flowchart 400 can include only an executable algorithm for the processor and including navigation within the distorted field is merely for clarity of the current discussion. In particular, once the distorted field is determined and the identified no-navigation volumes are determined in blocks 418 and 420, the navigation system 20 can be operated to navigate the procedure 430. Accordingly, it is understood that the act of determination or evaluation of the distorted field for navigation can end in block 418 without requiring navigation of a procedure.

In an alternative, if it is determined that the accessed or entered configuration is not identical to a saved configuration in block 410 then a no-path through block 450 can be followed. As a first option, the configuration of the head holder can be accessed, as with the position sensor 310 from block 406. The configuration of the head holder 100 can, therefore, be sensed with the sensor 310. Alternatively, the measured configuration of the head holder 100 by the user 21 can be entered in block 406. The accessed or entered configuration of the head holder 100 can then be used to calculate a distorted field based on the accessed or entered configuration and a known location of the localizer 110*a* in block 454.

By determining a configuration of the head holder 100 during a procedure, the distortion of the generated field can be determined based upon the determined configuration of the head holder 100 and materials of the head holder 100. In one example, the processor 42 can interpolate between known distorted field parameters at the saved configurations (e.g. angles of the arms 140, 142) of the head holder 100. Also, interpolation of distortion can be made between saved different configurations of the head holder 100. According to various embodiments, the distorted field could be analyzed and distorted field parameters may be stored and recalled for a subset of possible configurations. The subset of possible configurations can allow the determination of the distorted field parameters for any (e.g. all possible) selected configuration. For example, if a saved configuration includes angles of 10 degrees and 12 degrees and the measured angle is 11 degrees, an interpolated distorted field parameter can be determined by the processor 42.

In further explanation, interpolation can include interpolating a navigation field, which can be the distorted generated field, based on the determined configuration of the head holder 100, or other selected configurable theater system that is saved (e.g. saved in an accessible database). Saved in the database can be at least two navigation fields based on at least two different configurations of the configurable theater system and/or at least two different configurations of the head holder 100. The interpolated (e.g. calculated with the processor based on the accessed navigation fields and/or configurations) navigation field and/or configuration can then be used to determine distorted field parameters for the specific and particular configuration of the head holder. Thus, all possible configurations and/or distorted field parameters do not need to be determined prior to a procedure, but the processor can interpolate between predetermined configurations and/or distorted field parameters.

In addition to interpolating the distorted field parameters, the current configuration may also be interpolated. The interpolation may be based upon receiving with the processor a signal from a position sensor, such as the angle sensor 310, a signal relating to a configuration of the head holder 100. The signal can be used to interpolate a specific and current configuration of the head holder based predetermined signals related to configurations of the head holder.

In a further example, the calculation by the processor 42 can be based upon known algorithms and effects of the materials of the head holder 100 on the field generated by the localizer 110*a*. In other words, the known materials and configuration of the materials relative to the localizer 110*a* can be used to calculate distorted field parameters based on the entered configuration from block 406.

The calculated distortion, according to various examples including interpolation or field distortion calculations, can be used for navigation in the same way as a factory calibrated distortion field parameter which can be recalled in block 418. However, the calculation will be determined during use or following physically configuring the head holder 100 by a user during or immediately prior to a procedure. Nevertheless, the calculation of the distorted field in block 454 can be used for navigation and also can be used for identifying no-navigation volumes in block 420. Navigation of a procedure can then occur in block 430, as discussed above, and the procedure can end at block 440.

As an alternative when following a no-path 450, a sensed distorted field parameter by one or more field sensors 462 on the head holder 100 or relative to the head holder in block 460 can be used. The distorted field can be sensed substantially directly with the field sensors 462 associated with or placed on the head holder 100. The field sensors, such as the field sensor 462, illustrated in FIGS. 3A and 3B, can be used to sense a distorted field based on a field generated by the localizer 110*a* that is distorted by the head holder 100. The field sensors may be similar to those disclosed in U.S. Pat. No. 7,313,430, incorporated herein by reference. The field sensed with the field sensors 462 in block 460 can be used to determine the distorted field of the localizer 110*a*. Sensing the distorted field with the sensors 462 can be substantially similar to a factory calibration technique where the generated field is sensed and/or measured at various locations (e.g. near where navigation is to occur) to determine the navigation field which can include distortions due to the material of the head holder 100. The sensed distorted field can then be used to determine no-navigation volumes in block 420. The distorted field can be used to navigate the procedure 430, as discussed above and the procedure or the procedure can end in block 440.

Accordingly, active or adaptive procedures, including an algorithm that can be executed by a processor, such as one associated with a work station, can be used to assist in determining or navigating with a distorted field due to a configuration of the head holder 100. Again, it is understood that the head holder 100 discussed in the flowchart 400 can be exemplary of any appropriate device that is used during an operative procedure. For example, a configuration of the operating room bed 112, position of the imaging device 128, or other items that may disturb the field can be entered into an algorithm for calculating a distorted field or considered when determining the parameters of the distorted field for navigation in block 430.

Moreover, as discussed above, the localizer 110*a* can be connected to the head holder 100 in a selected manner. For example, the localizer 110*a* can be clamped to the head holder 100 in a specific and repeatable location and orientation, such as with a clamp that engages the head holder 100 in a substantially single specific location and orientation. It is also understood, however, that the localizer 110*a* can be formed to be substantially permanently connected to the head holder 100, such as with welding, brazing or other fixed configurations. Accordingly, the head holder 100 may not be formed with the localizer 110*a*, but can be designed or manufactured such that the localizer 110*a* is substantially permanently connected to the head holder 100 through substantially known permanent techniques (e.g., welding, brazing, etc.).

It is also understood that the localizer 110*b*, as illustrated in FIG. 2, can be incorporated directly into a portion of the head holder 100. For example, as discussed above and illustrated in FIG. 2, the head holder 100 can include parts that are substantially non-distorting, such as the non-distorting part 190. The localizer 110*b* can be formed to be integrally provided with the non-distorting part 190. For example, the non-distorting part can be a polymer that can be molded into the configuration for forming the head holder 100. The localizer 110*b* can be molded into the non-distorting part 190 during a manufacturing process, such as an injection or investment molding. Further, the non-distorting part 190 can include a pocket or opening that can receive the localizer 110*b* in a substantially single configuration and location relative to the non-distorting part 190. Thus, the localizer 110*b* can be fixed within a boundary of the non-distorting part 190. Accordingly, it is understood, that the localizer 110*b* can be provided within a boundary of the members forming the head holder 100 and need not be attached exteriorly thereto.

It is further understood that the localizers 110*a* and 110*b* can be positioned in the head holder 100 in any appropriate or selected configurations or locations. The localizers 110*a* and 110*b* illustrated in FIG. 2 are merely exemplary of locations and configurations of the localizers 110*a* and 110*b*. For example, as discussed above, the localizers 110*a* and 110*b* can include a plurality of coils in the coil array 52*a*. The plurality of coils, however, can be individually positioned within the head holder 100 to form an array that is at least in part oriented relative to or with the head holder portions. Accordingly, it is understood that the coil array 52*a* of the localizers need not be integrated into a single unit as illustrated in FIG. 2, but can be provided at several locations on the head holder 100 separately.

As discussed above, a geometry of one or more of the members of the head holder 100, such as the arms 140, 142 can affect the generated field. Thus, a geometry of at least one member of the head holder, such as one of the arms 140, 142, may be designed to minimize distortions of the generated undistorted electromagnetic field. For example, a geometry of the arms 140 can be selected to minimize distortions due to the geometry of the arm relative to the localizer 110*a*. Also, portions of the head holder 100, such as one or more of the materials of the arms 1402, 142 can include a magnetic feature to minimize distortions of the generated undistorted electromagnetic field. A magnetic feature can include a magnetic material or shielding. Also, the localizer may be designed to minimize distortions of the generated undistorted electromagnetic field when attached to the head holder 100. For example, case shape, coil position and/or number, etc. can be selected to minimize field distortions.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system to diminish the effects of distortion of a configurable theater system, comprising:
   a configurable theater system having a plurality of members including at least a first member movably interconnected relative to a second member and at least one head holding member extending from the first member, wherein the at least one head holding member is configured to engage a head;
   a localizer fixed into at least one of the first member or the second member of the configurable theater system at a single selected location, wherein the localizer is configured to generate an undistorted electromagnetic field; and
   a processor system configured to recall from a memory system a distorted field parameter based on a configuration of the configurable theater system that forms a distorted field that distorts the undistorted electromagnetic field, the processor system further configured to execute instruction to:
      access a determined configuration of the configurable theater system;
      recall from a saved database the distorted navigation field based on the accessed determined configuration of the configurable theater system;
      recall from a saved database a no-navigation volume based on the distorted navigation field based on the accessed determined configuration of the configurable theater system; and
      provide feedback to a user when the tracking device is in the no-navigation volume.

2. The system of claim 1, wherein at least a first part of the first member and a second part of the second member are formed of a first material and at least a third part of the first member and fourth part of the second member are formed of a second material different than the first material.

3. The system of claim 2, wherein at least one of the first part, the second part, the third part, or the fourth part of the configurable theater system is formed of a material to minimize distortion of the field generated by the localizer.

4. The system of claim 3, wherein the first member of the configurable theater system is formed as a single piece of both the first part and the third part and wherein only the second material has substantially no distorting effect on the generated undistorted electromagnetic field.

5. The system of claim 1, further comprising:
   a shield configured to substantially shield the generated undistorted electromagnetic field from a distorting effect of the configurable theater system.

6. The system of claim 1, wherein the localizer is selectively attached to the configurable theater system in a single location and orientation relative to at least one member of the plurality of members of the configurable theater system.

7. The system of claim 1, wherein at least one member of the plurality of members of the configurable theater system is formed of a moldable material and the localizer is molded within the at least one member of the plurality of members.

8. The system of claim 1, further comprising:
   a tracking device associated with an instrument;
   wherein the tracking device is configured to sense at least one of the generated undistorted electromagnetic field from the localizer or the distorted field;
   wherein the processor system is configured to execute instructions to determine a precise location of the tracking device with at least one of the generated undistorted electromagnetic field from the localizer or the distorted field due to distortion of the generated field by the configurable theater system.

9. The system of claim 1, wherein a geometry of at least one member of the plurality of members of the configurable theater system is to minimize distortions of the generated undistorted electromagnetic field.

10. The system of claim 1, wherein at least one member of the plurality of members of the configurable theater system includes a magnetic feature to minimize distortions of the generated undistorted electromagnetic field.

11. The system of claim 1, wherein the localizer reduces distortions of the generated undistorted electromagnetic field when attached to the configurable theater system.

12. The system of claim 1, wherein the distorted field parameter is saved in the memory system to be accessed by the processor system;
   wherein the distorted field parameter is due to selectable configurations of the configurable theater system;
   wherein the distorted field parameter is a parameter of the distorted field that has been distorted by the configurable theater system.

13. The system of claim 12, further comprising:
   a position sensor to determine a relative position of the first member relative to the second member of the configurable theater system;
   wherein the position sensor is configured to generate a position signal of a position of the first member relative to the second member of the configurable theater system and transmit the position signal to the processor system.

14. The method of claim 12, wherein the storing in a memory system at least one distorted field parameter defining a distorted field based on each configuration of a configurable theater system of a plurality of configurations of the configurable theater system is determined and stored during a factory calibration.

15. A method of tracking a tracking device, comprising:
   moving a first member of a configurable theater system relative to a second member of the configurable theater system to configure the configurable theater system into one configuration of a plurality of configurations;
   operating a localizer to generate an electromagnetic field, wherein the generated electromagnetic field is affected by the configurable theater system to form a distorted navigation field, wherein the distorted navigation field is distorted from the generated electromagnetic field by the configurable theater system;
positioning a tracking device to sense the distorted navigation field near the configurable theater system; and
operating a processor system to determine a location of the tracking device that is sensing the distorted navigation field,
wherein operating the processor system includes:
accessing a determined configuration of the configurable theater system;
recalling from a saved database the distorted navigation field based on the accessed determined configuration of the configurable theater system;
recalling from a saved database a no-navigation volume based on the distorted navigation field based on the accessed determined configuration of the configurable theater system; and
providing feedback to a user when the tracking device is in the no-navigation volume.

16. The method of claim 15, further comprising:
receiving with the processor system a signal from a position sensor associated with the configurable theater system that indicates the configuration of the configurable theater system selected from a plurality of configurations of the configurable theater system.

17. The method of claim 16, wherein operating a processor system includes:
accessing a determined configuration of the configurable theater system based on the received signal with the processor system from the position sensor; and
interpolating the navigation field based on the accessed determined configuration of the configurable theater system and a saved database of at least two navigation fields based on at least two different configurations of the configurable theater system.

18. The method of claim 15, further comprising:
forming the configurable theater system from a first material and a second material; wherein at least one of the first material has substantially no distorting effect on the electromagnetic field;
wherein the first member is formed as one piece having a first part of the first material and a second part of the second material distinct from the first part.

19. The method of claim 18, wherein at least the first material is at least one of a non-conducting material or non-magnetic material and different from the second material.

20. The method of claim 19, further comprising integrating the localizer into at least the first member includes molding the localizer into the first part.

21. The method of claim 15, further comprising:
selectively fixing the localizer to the configurable theater system in a selected location and selected orientation that is repeatable to allow for determination of the distorted navigation field during a first calibration period and a second procedure period that is later in time than the first calibration period.

22. The method of claim 15, further comprising:
receiving with the processor system a signal from a position sensor associated with the configurable theater system that indicates the configuration of the configurable theater system based on a position of the first member relative to the second member determined from at least a plurality of configurations of the configurable theater system.

23. A system to diminish the effects of distortion of a configurable theater system, comprising:
a configurable theater system having:
a first member formed of a first material, and
a second member moveably connected to the first member and formed of a second material,
wherein the first member and the second member are selectively moveable relative to one another to form a plurality of configurations of the configurable theater system;
a localizer immovably connected to the configurable theater system at a single selected location, wherein the localizer is configured to generate an undistorted electromagnetic field that is distorted to a distorted field by at least one of the first member or the second member of the configurable theater system;
a memory system having stored thereon at least one distorted field parameter regarding each configuration of the plurality of configurations to distort the undistorted field to the distorted field that is distorted by at least one of the first member or the second member the configurable theater system;
a first configuration sensor associated with the configurable theater system configured to transmit a signal to the processor system based on sensing the distorted field due to a current configuration of the configurable theater system, wherein the processor system is configured to execute instructions to determine based at least on a recall from the memory system a specific distorted field parameter based of the at least one distorted field parameter on the transmitted signal; and
a second configuration sensor associated with the configurable theater system configured to transmit a signal to the processor system indicating an angle between the first member and the second member based on the current configuration of the configurable theater system;
a processor system configured to execute instructions to recall from the memory system the at least one distorted field parameter based on a current configuration of the plurality of configurations of the configurable theater system.

24. The system of claim 23,
wherein the processor system recalls from the memory system a specific distorted field parameter of the at least one distorted field parameter based on the transmitted signal regarding the current configuration of the configurable theater system.

25. The system of claim 24, further comprising:
a tracking device configured to sense the distorted field;
wherein the processor is configured to execute instructions to determine a location of the tracking device based on the sensed distorted field and the recalled specific distorted field parameter.

26. The system of claim 25, further comprising:
an instrument;
wherein the tracking device is associated with the instrument and the processor system is configured to determine a location of the instrument based on the determined location of the tracking device sensing the distorted field.

27. The system of claim 24, wherein the first material is different from the second material;
wherein the first material is a non-conductive material and non-magnetic.

28. The system of claim 23, further comprising:
a tracking device configured to sense the distorted field;
wherein the processor system determines a location of the tracking device based on the sensed distorted field and the recalled specific distorted field parameter.

29. The system of claim 28, wherein the processor system determines the configuration of the configurable theater system based on the sensed distorted field with the tracking device and the at least one distorted field parameter recalled from the memory system.

30. A method to diminish the effects of distortion of a configurable theater system, comprising:
storing in a memory system at least one distorted field parameter defining a distorted field based on each configuration of a configurable theater system of a plurality of configurations of the configurable theater system to define a distorted field that is distorted by the configurable theater system in each configuration of the configurable theater system;
receiving with a processor system a first signal of a field sensor associated with the configurable theater system based on the distorted field;
receiving with the processor system a second signal from a configuration sensor associated with the configurable theater system configured to indicate an angle between a first member and a second member of the configurable theater system;
determining a current configuration of the configurable theater system based at least on the first signal or the second signal;
determining if the determined current configuration of the configurable theater system matches at least one configuration of the plurality of configurations of the configurable theater system for which at least one distorted field parameter is defined; and
recalling with a processor system from the memory system the at least one distorted field parameter.

31. The method of claim 30, further comprising:
determining a location of a tracking device sensing the distorted field based on the recalled distorted field parameter based on the current configuration.

32. The method of claim 31, further comprising:
providing the configurable theater system to have:
the first member formed of a first material, and
the second member moveably interconnected to the first member and formed of a second material,
wherein the plurality of configurations include at least the first member and the second member at selected positions relative to one another to form the plurality of configurations of the configurable theater system.

33. The method of claim 31, further comprising:
immovably connecting a localizer to the configurable theater system at a single selected location, wherein the localizer is configured to generate an undistorted electromagnetic field that is distorted by at least one of the first member or the second member of the configurable theater system.

34. The method of claim 33, further comprising:
determining the distorted field parameter at each configuration of the plurality of configurations.

35. The method of claim 30,
moving the configurable theater system into at least one configuration of the plurality of configurations of the configurable theater system;
wherein recalling the at least one distorted field parameter is based on the determined configuration of the configurable theater system.

36. The method of claim 30, wherein determining the current configuration of the plurality of configurations of the configurable theater system includes:
determining that the current configuration does not match at least one configuration of the plurality of configurations of the configurable theater system for which at least one distorted field parameter is defined;
sensing the distorted field with a tracking device; and
determining the current configuration of the configurable theater system based on the sensed distorted field and the recalled at least one distorted field parameter.

* * * * *

UNITED STATES PATENT AND TRADEMARK OFFICE
CERTIFICATE OF CORRECTION

PATENT NO.        : 9,854,991 B2
APPLICATION NO.   : 13/833452
DATED             : January 2, 2018
INVENTOR(S)       : Bzostek et al.

Page 1 of 1

It is certified that error appears in the above-identified patent and that said Letters Patent is hereby corrected as shown below:

In the Claims

Column 22, Line 53, Claim 14 delete "method" and insert --system-- therefor.

Signed and Sealed this
Fifteenth Day of May, 2018

Andrei Iancu
*Director of the United States Patent and Trademark Office*